(12) United States Patent
Hall et al.

(10) Patent No.: US 9,986,879 B2
(45) Date of Patent: Jun. 5, 2018

(54) ANTIMICROBIAL SELF-CLEANING TOILET

(71) Applicants: David R. Hall, Provo, UT (US); Steven J. M. Butala, Provo, UT (US); Jared Reynolds, Pleasant Grove, UT (US); Joshua Larsen, Spanish Fork, UT (US); Joe Fox, Spanish Fork, UT (US)

(72) Inventors: David R. Hall, Provo, UT (US); Steven J. M. Butala, Provo, UT (US); Jared Reynolds, Pleasant Grove, UT (US); Joshua Larsen, Spanish Fork, UT (US); Joe Fox, Spanish Fork, UT (US)

(*) Notice: Subject to any disclaimer, the term of this patent is extended or adjusted under 35 U.S.C. 154(b) by 0 days. days.

(21) Appl. No.: 15/664,045

(22) Filed: Jul. 31, 2017

(65) Prior Publication Data
US 2018/0008106 A1   Jan. 11, 2018

Related U.S. Application Data

(63) Continuation-in-part of application No. 15/201,822, filed on Jul. 5, 2016, now Pat. No. 9,737,181.

(51) Int. Cl.
| | |
|---|---|
| *A47K 13/14* | (2006.01) |
| *E03D 5/10* | (2006.01) |
| *E03D 11/02* | (2006.01) |
| *E03D 5/00* | (2006.01) |
| *A47K 13/24* | (2006.01) |
| *E03D 9/00* | (2006.01) |
| *A61L 2/08* | (2006.01) |

(52) U.S. Cl.
CPC .............. *A47K 13/24* (2013.01); *A61L 2/088* (2013.01); *E03D 5/00* (2013.01); *E03D 9/005* (2013.01); *E03D 11/02* (2013.01); *A61L 2202/17* (2013.01)

(58) Field of Classification Search
CPC .......... A47K 13/24; E03D 5/00; E03D 9/005; E03D 11/02; A61L 2/088; A61L 2202/17
USPC ..................................................... 4/300, 420
See application file for complete search history.

(56) References Cited

U.S. PATENT DOCUMENTS

| | | | |
|---|---|---|---|
| 2008/0134420 A1* | 6/2008 | Ho ........................ | A47K 13/302 4/233 |
| 2014/0115764 A1* | 5/2014 | Cheng .................. | A47K 13/302 4/222 |

* cited by examiner

*Primary Examiner* — Tuan N Nguyen

(57) ABSTRACT

A toilet comprising a rinsing seat, a rimless bowl, and a helical loop trapway is disclosed. An annular cavity for the purpose of storing and dispensing rinse water from the rinsing seat is disclosed. Outlet nozzles arranged about the circumference of the rinsing seat and designed to dispense rinse water at the rimless bowl are disclosed. Rinsing seat supports, hinge assemblies, and seat sensors which offer additional functionality to the rinsing seat are also disclosed. The toilet includes a steep interior surface with a titanium dioxide coating and actuatable ultraviolet light sources. The titanium dioxide has antimicrobial properties in the presence of ultraviolet light to sanitize the toilet. The ultraviolet light source is actuatable to control when the antimicrobial properties of the titanium dioxide coating are activated. The exterior of the toilet is coated with doped titanium dioxide which is antimicrobial in the presence of visible light.

20 Claims, 11 Drawing Sheets

ANTIMICROBIAL SELF-CLEANING TOILET

CROSS REFERENCE TO RELATED APPLICATIONS

This application is a continuation-in-part of co-pending U.S. patent application Ser. No. 15/201,822 filed on Jul. 5, 2016 which is hereby incorporated by reference in its entirety.

FIELD OF THE INVENTION

This invention relates to toilets, and, in particular, to toilets having self-cleaning properties and apparatuses and antimicrobial properties.

BACKGROUND OF THE INVENTION

Conventional toilets have a rim around the perimeter of the toilet bowl in order to flush the toilet. Such toilets are difficult to clean due to the overhanging rim that protrudes into the toilet bowl space. Rim toilets also have many orifices in order to rinse and flush the toilet. These orifices are easy targets for bacterial growth and frequently stain. Rimless toilets are currently available which boast easier cleaning and more effective flushing. However, even these rimless toilets have orifices in the toilet bowl which are prone to staining from iron or sediment deposits from water used in the toilet. A large rim also adds thickness to the toilet bowl, thus reducing the open area for capturing urine from standing urination and increasing the frequency with which urine is sprayed or splashed onto the toilet rim.

Rim rinsing requires large amounts of water to rinse excrement adhered to the bowl, and is often ineffective in that goal. In addition, rim rinsing requires the bowl to have a non-steep bowl wall so that rim rinse water can more effectively clean the bowl, and non-steep bowl walls are a primary cause and location for streaks or so called "skid marks" caused by excrement. Rim rinse water detracts from the amount of water per flush that can be used for the flushing jet, which creates many engineering design constraints for a toilet that lead modern low flush volume toilets to have narrower or longer trapways that are more easily clogged. Rim rinse water is often not separate from flush water. Thus, rim rinsing requires disinfecting or cleaning agents to either be used in all rinse and flush water. Otherwise, disinfecting or cleaning agents must be applied to the toilet manually by external means.

In addition, there are situations in which it is desirable to temporarily preserve the microbes in a user's excrement. In one example, it may be desirable to collect a sample to be analyzed for medical purposes as may be done when the toilet is a medical toilet. The medical toilet may include instruments to perform measurements related to a user's health. Another example is when the excrement is transferred to a digester for use in producing clean energy. In this example, it is desirable for the microbes to be alive when the excrement reaches the digester. After flushing, it is then desirable to kill microbes remaining in the toilet bowl and on exterior surfaces of the toilet.

What is needed is a toilet without a rim at all in order to decrease bowl thickness and increase the area for capturing human waste. Furthermore, what is needed is a means of separating rinse water from flush water, so that disinfecting or cleaning agents may be used at a minimum, which is ecologically preferred, material saving, and more energy efficient. In addition, what is needed is a toilet utilizing bowl and trapway designs which minimize the likelihood of streaks or stains and clogs respectively. Ideally, such improvements in a toilet would increase toilet cleanliness, reduce cleaning frequency, and possess antimicrobial properties which are actuated in a controlled manner.

SUMMARY

This invention has been developed in response to the present state of the art and, in particular, in response to the problems and needs in the art that have not yet been fully solved by currently available systems. Accordingly, an improved toilet has been developed. Features and advantages of different embodiments of the invention will become more fully apparent from the following description and appended claims, or may be learned by practice of the invention as set forth hereinafter.

Consistent with the foregoing, a toilet comprising a rinsing seat, rimless bowl, and helical loop trapway is disclosed. The rinsing seat has an annular cavity and outlet nozzles arranged circumferentially so that rinse water can be dispensed through the rinsing seat and directed to the rimless bowl. The rimless bowl provides a continuous, smooth surface, which dramatically increases ease of cleaning. Steep walls and hydrophobic walls are disclosed, which reduce the inconveniences caused by excrement streaks. The helical loop trapway is shown to comprise a jet to facilitate flush initiation. Seat supports having interior cavities for the passage of water tubes or pipes are disclosed. A motorized hinge assembly and various sensors are disclosed which may allow the rinsing seat to function autonomously in response to a toilet user's movement, position, or bio data. A pressurized line and disinfectants which may increase the rinsing seat's cleaning effectiveness are also disclosed and claimed herein.

The rimless bowl may include a titanium dioxide coating. An ultraviolet light source may direct ultraviolet light toward the interior surface of the rimless bowl. The ultraviolet light source may be actuatable, for example, with a switch so that a user may control when the ultraviolet light source activates the antimicrobial properties of the titanium dioxide coating.

The exterior of the toilet may include a doped titanium dioxide coating which has antimicrobial properties in the presence of visible light. The doped titanium dioxide may include one or more of nitrogen, carbon, phosphorus, sulfur, fluorine, noble metals, and transition metals.

BRIEF DESCRIPTION OF THE DRAWINGS

In order that the advantages of the invention will be readily understood, a more particular description of the invention briefly described above will be rendered by reference to specific embodiments illustrated in the appended drawings. Understanding that these drawings depict only typical embodiments of the invention and are not therefore to be considered limiting of its scope, the invention will be described and explained with additional specificity and detail through use of the accompanying drawings, in which.

DETAILED DESCRIPTION

It will be readily understood that the components of the present invention, as generally described and illustrated in the Figures herein, could be arranged and designed in a wide variety of different configurations. Thus, the following more detailed description of the embodiments of the invention, as represented in the Figures, is not intended to limit the scope of the invention, as claimed, but is merely representative of certain examples of presently contemplated embodiments in accordance with the invention. The presently described embodiments will be best understood by reference to the drawings, wherein like parts are designated by like numerals throughout.

Figure 1:
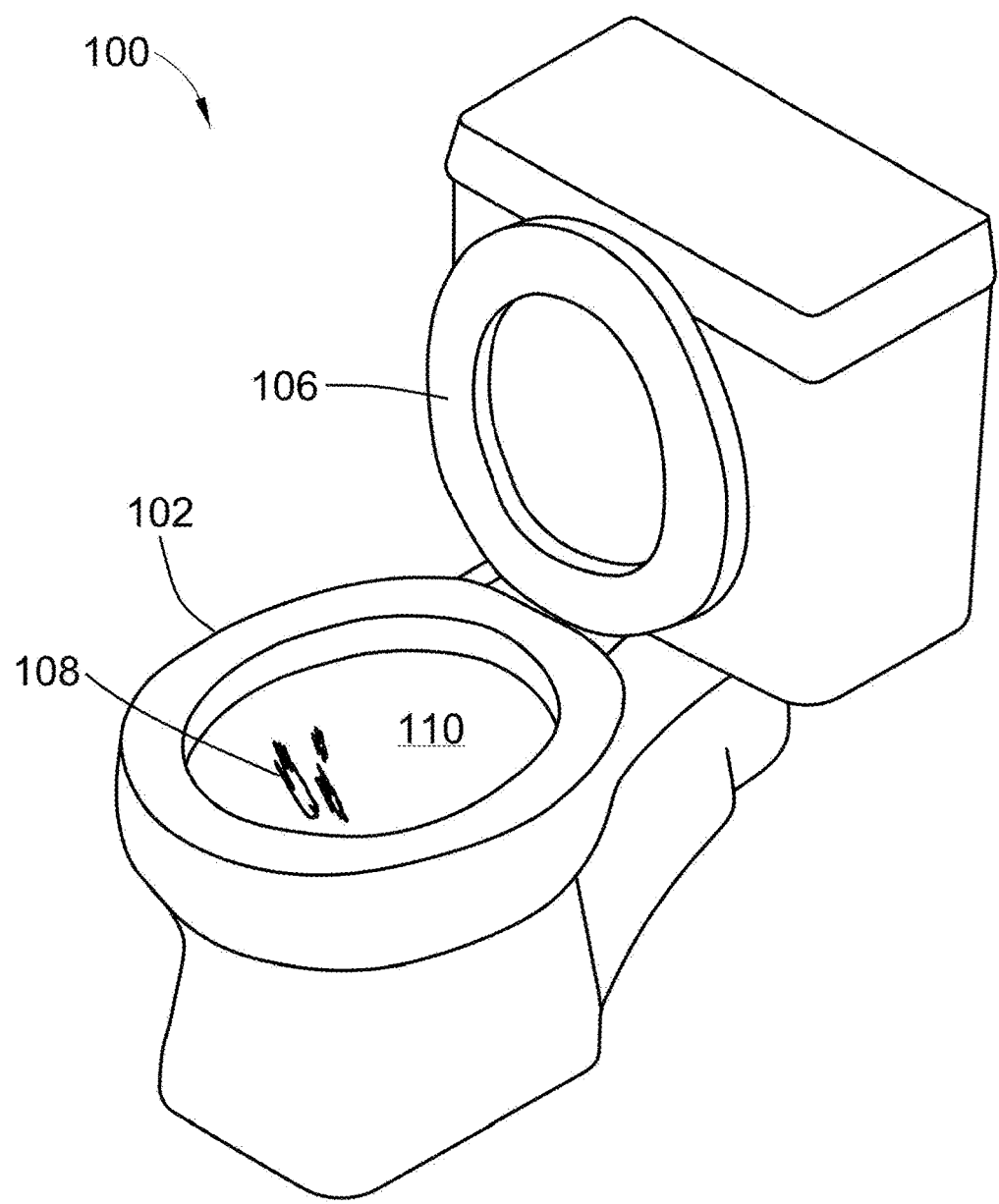
FIG. 1 shows a perspective view of a prior art toilet.

Referring to FIG. 1, a toilet 100 currently found in the prior art is shown. The toilet 100 comprises a rimmed top 102 and a seat 106. The toilet 100 also comprises a non-steep bowl 110, the non-steep bowl 110 shown having streak marks 108 caused by human waste striking the non-steep bowl 110. The occurrence of streak marks 108 is common in the art and is detrimental to the cleanliness of the toilet 100 if not removed by rinse water from the rimmed top 102 or by external means. The presence of streak marks 108 also detracts from toilet user experience by causing odors, facilitating the buildup of more waste in the non-steep bowl 110, and decreasing the comfort level of a toilet user. The presence of streak marks 108 is particularly undesirable if left uncleaned for long periods of time, which allows the streak marks 108 to solidify and become more difficult to clean.

Figure 2:
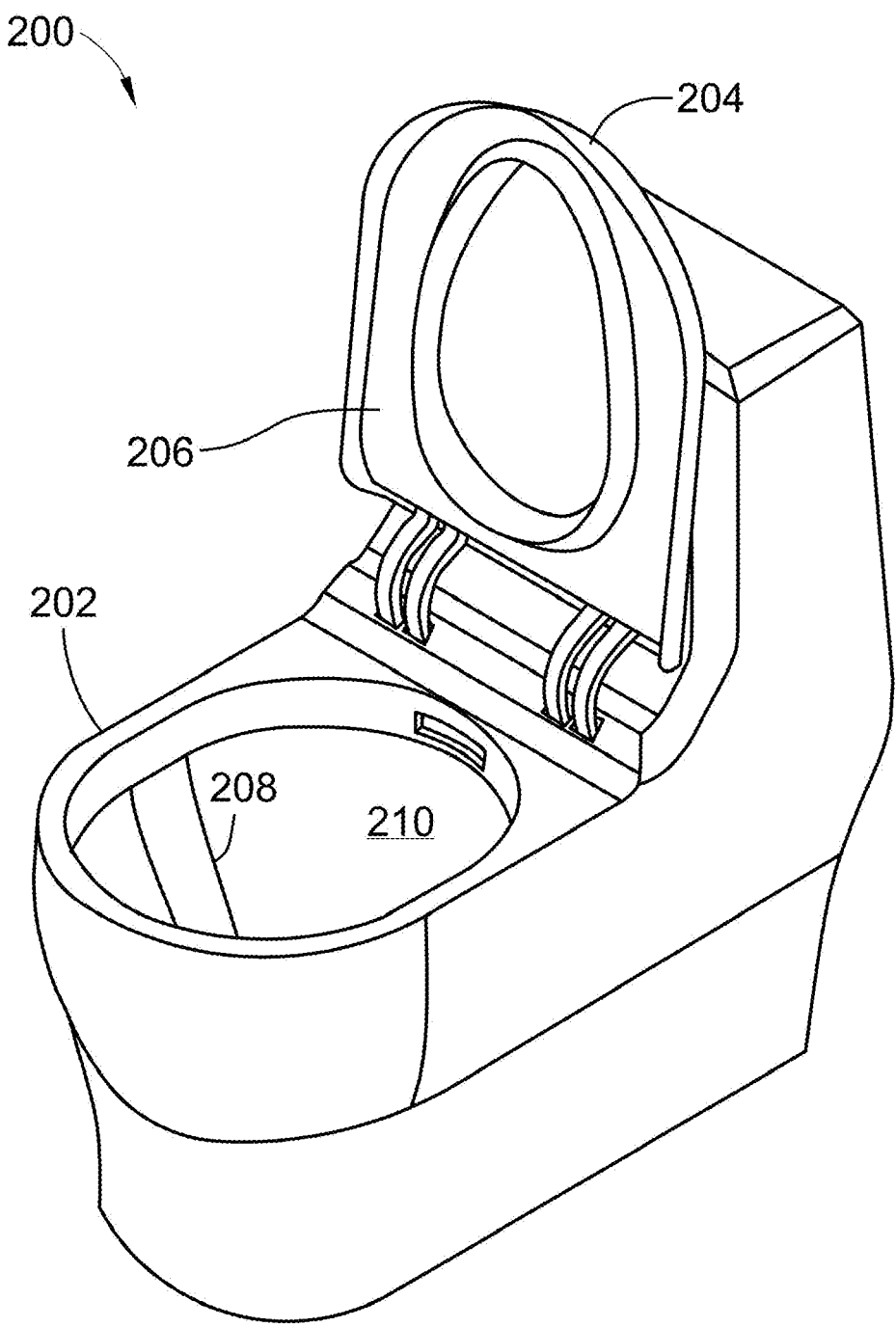
FIG. 2 shows a perspective view of a rimless bowl toilet of the present invention.

FIG. 2 shows a toilet 200 of the present invention. The toilet 200 comprises a rimless bowl 210 having a rimless top 202. The rimless bowl 210 may provide a larger opening for capturing waste by eliminating the need for a rim. The rimless bowl 210 also provides for an interior portion of the toilet which is easier to clean because it has no rim, ledges, orifices, or concave corners. The rimless top 202 may also be thinner than a traditional rimmed toilet top. The rimless bowl 210 is shown comprising steeply sloped bowl walls 208. The size and thus the volume of excrement streaks left in a toilet bowl are larger when the angle of incidence of a piece of excrement is larger. Thus, steeply sloped bowl walls 208 reduce the size and likelihood of excrement streak formation in the rimless bowl 210. The rimless bowl 210 may also comprise a hydrophobic surface which also reduces the size and likelihood of excrement streak formation. The toilet 200 is also shown comprising a rinsing seat 206 and a lid 204, both of which are shown and described hereafter in FIG. 6. The toilet 200 comprises a concealed water tank for storing and dispensing a flushing volume of water into a helical loop trapway in a manner shown hereafter in FIG. 7 and FIG. 8.

Figure 3:
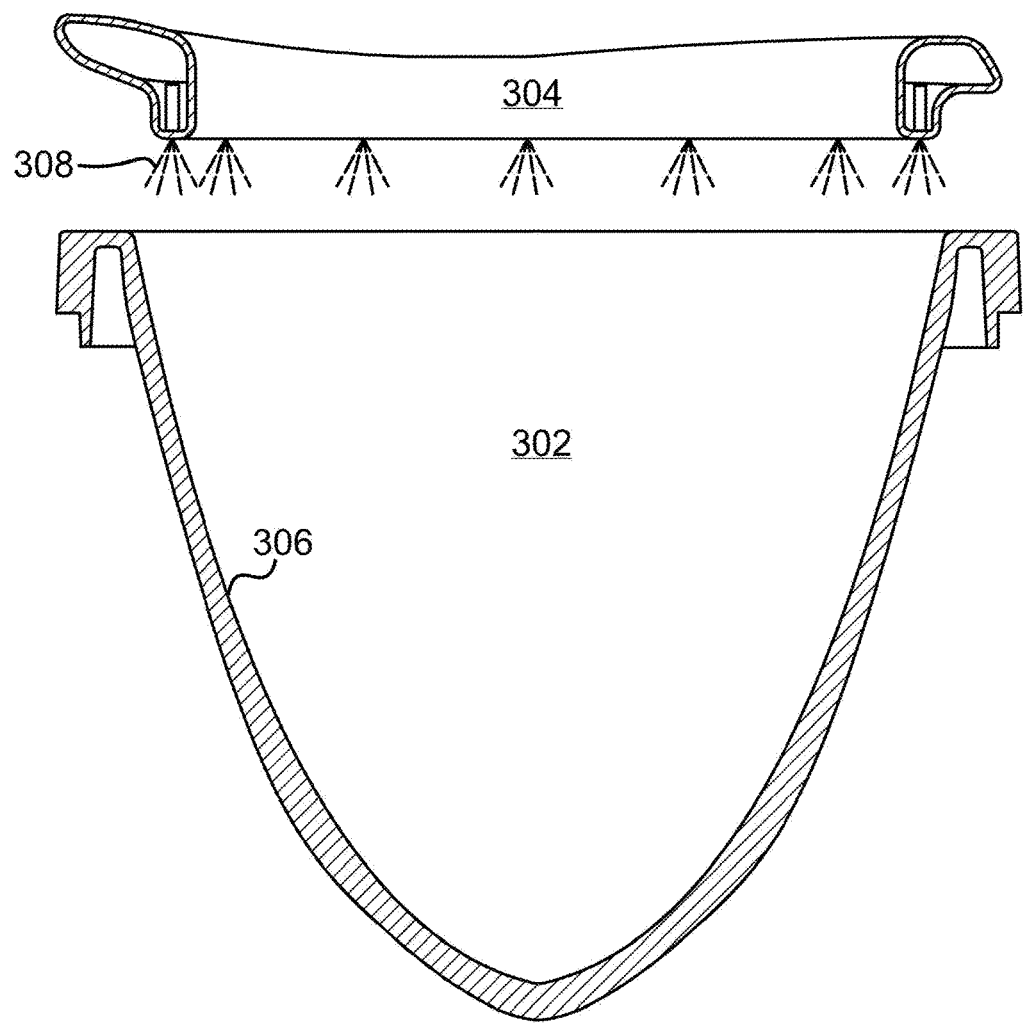
FIG. 3 shows a rinsing seat dispensing rinse water into a rimless bowl.

FIG. 3 shows a cross-sectional view of a rimless bowl 302 and a rinsing seat 304 with a hollowed annular cavity of the present invention. The rinsing seat 304 is positioned above the rimless bowl 302 and is shown dispensing rinse water 308 directed to the rimless bowl 302. The rimless bowl 302 is shown having a steep interior wall 306 so that the incident angle of excrement passed from a user into the rimless bowl 302 is reduced in comparison to the non-steep interior walls of traditional toilets. The rinse water 308 may be dispensed by oscillating spray nozzles which spray the steep interior wall 306 in oscillatory motions, thus directing a focused jet of water at many locations and increasing cleaning effectiveness. The outlet nozzles may also dispense rinse water in an overlapping pattern to ensure that the entire circumference of the rimless bowl 302 is rinsed with enough pressure to clean the steep interior wall 306. The rinse water 308 comes from a remote water source which may be independently controllable from flush water used in a pressurized jet directed into a helical loop trapway to initiate and carry out a flush. Thus, the rinse water 308 may be dispensed at any time, including before, during, or after a toilet flush. Disinfectants may be combined with the remote water source such that the rinse water 308 comprises disinfecting properties, deodorizing properties, or a combination thereof. The disinfectants may comprise an oxidizer, ozone, a bleaching chemical, or a combination thereof. The rinse water 308 may be dispensed in the form of a liquid or a foam.

Figure 4A:
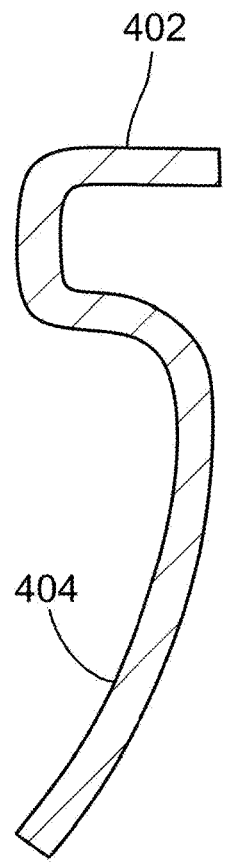
FIGS. 4A and 4B show cross-sectional views of a rimmed toilet and rimless toilet respectively.
Figure 4B:
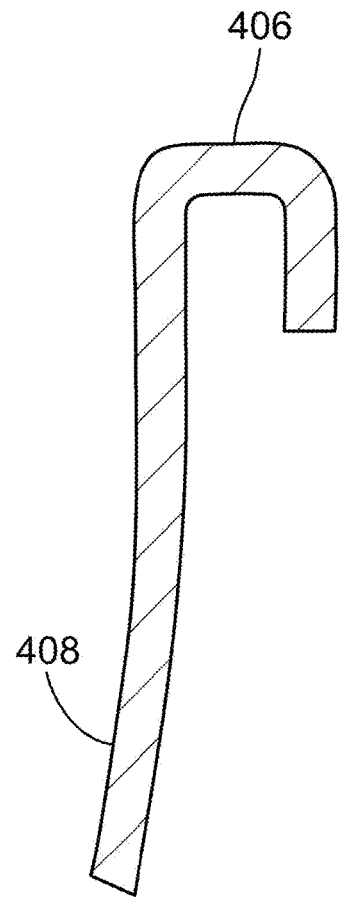

FIGS. 4A and 4B provide a comparison of a traditional rimmed toilet cross section (FIG. 4A) and a rimless bowl toilet cross-section of the present invention (FIG. 4B). FIG. 4A shows toilet bowl cross section having a rimmed top 402 and a non-steep bowl wall 404. The rimmed top 402 is required so that water may be dispensed from the rimmed top and downward along the non-steep bowl wall 404. The non-steep bowl wall 404 is required for a rimmed top 402 design because water must have sufficient adhesion along the non-steep bowl wall 404 surface to clean away any excrement or other waste adhered to the surface. FIG. 4B shows a rimless bowl cross-section of the present invention comprising a rimless top 406 and a steep wall 408. The rimless top 406 does not comprise orifices, exposed concave corners, or sharp edges which would be difficult to clean. Instead, the rimless top 406 and steep wall 408 provide a continuous, smooth surface for optimal ease of cleaning. The steep wall 408 reduced the size and likelihood of excrement streak formation on the interior rimless bowl surface.

Figure 5:
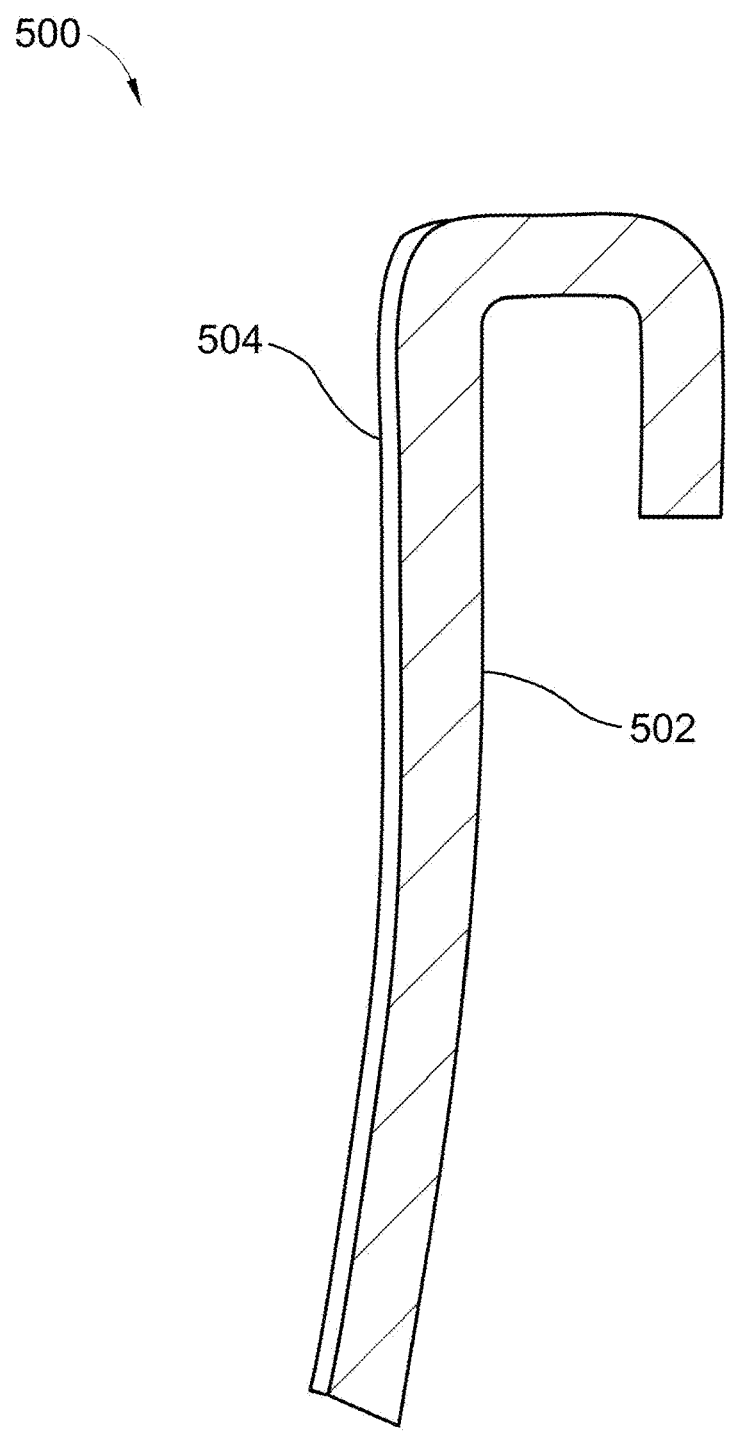
FIG. 5 shows a cross-sectional view of a rimless toilet bowl wall with a hydrophobic coating.

FIG. 5 shows a cross-sectional view of a hydrophobic rimless wall 500. The hydrophobic rimless wall comprises a rimless bowl wall 502 and a hydrophobic coating 504. The hydrophobic coating 502 is shown covering an interior surface of the rimless bowl wall, which would be exposed to a user when a user uses the toilet. The hydrophobic coating 502 may be applied to the rimless bowl wall 502 as a spray applied periodically to maintain hydrophobic properties. The hydrophobic coating 502 may be applied as a permanent coat to the rimless bowl wall 502. Alternatively, the hydrophobic rimless wall 500 may comprise a hydrophobic material which is integrated into the composition of the rimless bowl wall material. The hydrophobic coating 504 (or material) increases toilet cleanliness by preventing buildup of waste on a toilet bowl surface. In conjunction with a steep rimless bowl wall, the hydrophobic coating 504 further reduces the size and likelihood of excrement streak formation. As such, the hydrophobic coating 504 enables self-cleaning properties by inherently repelling waste that would otherwise adhere to the toilet bowl surface and require cleaning.

Figure 6:
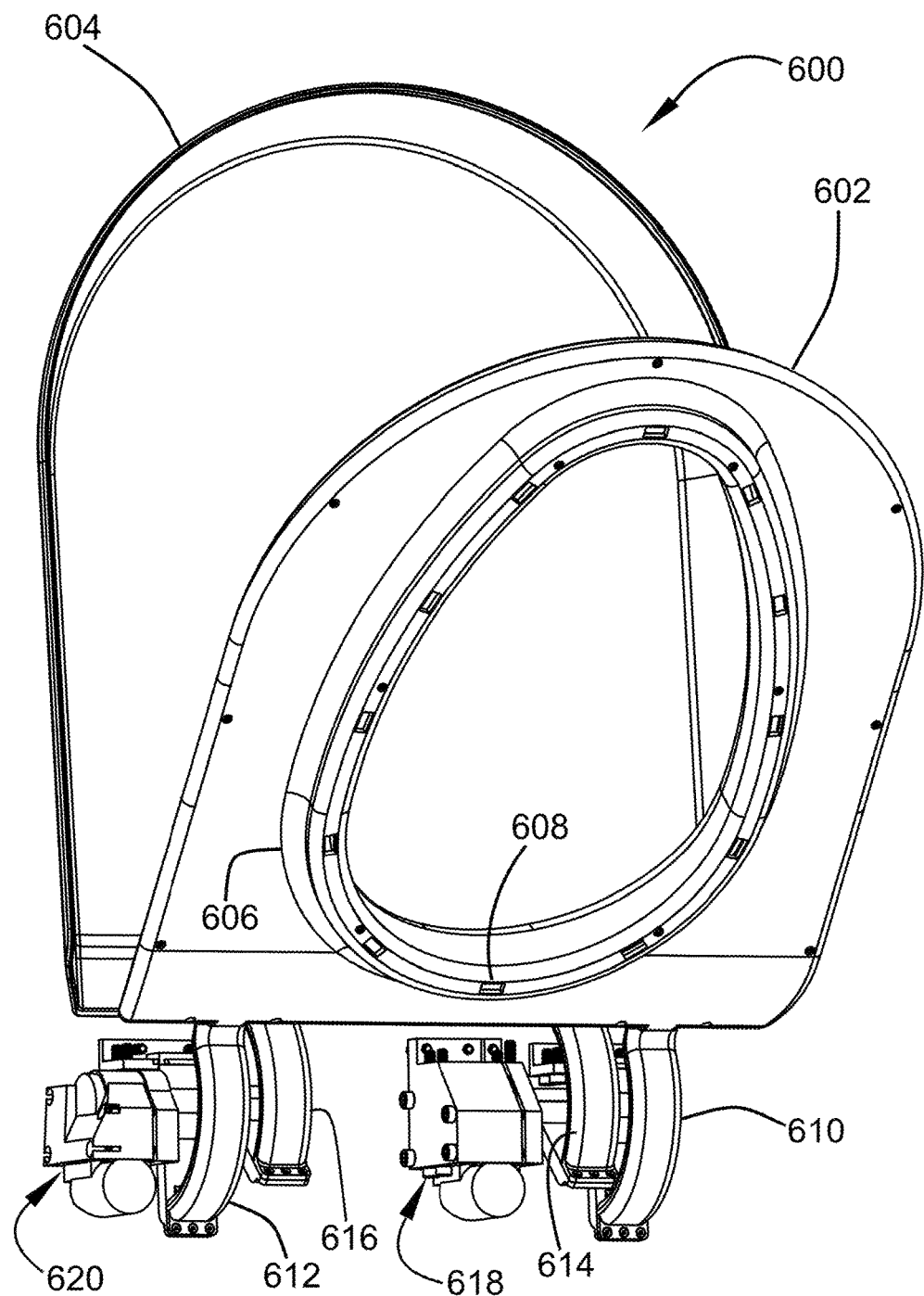
FIG. 6 shows rinsing seat and lid hingedly attached by arcuate supports to hinge assemblies.

FIG. 6 shows a toilet seat assembly 600 utilizing a rinsing seat 602. The rinsing seat 602 comprises an annular ridge 606 which extends about the circumference of the opening in the rinsing seat 602. The annular ridge 606 further comprises outlet nozzle openings 608 arranged circumferentially about the opening in the rinsing seat 602. The outlet nozzle openings 608 are pointed generally away from the rinsing seat 602 so that when the seat is in a down or closed position, the outlet nozzle openings 608 point generally downward directed into a toilet bowl. The rinsing seat 602 further comprises an annular cavity that extends about the circumference of the opening in the rinsing seat 602 in a manner similar to the annular ridge 606. The annular cavity comprises a volume sufficient to provide the outlet nozzle openings 608 with sufficient water to perform a bowl rinse, whether the water be pressurized, passed through water tubes, passed through water pipes, or passed through a cavity in the rinsing seat 602. The annular cavity may comprise a volume sufficient to pass between 0.1 to 1.6 gallons. For a brief rinsing or deodorizing rinse, the rinsing volume may comprise just 0.1 gallons, whereas the rinsing volume may also comprise a greater volume of 1 gallon for a deep clean of the toilet bowl. The rinsing volume may comprise up to 1.6 gallons such that the toilet can be fully flushed using only water dispensed from the rinsing seat. The rinsing seat 602 further comprises a first support 610 and a second support 612 at its base, the first support 610 being hingedly attached to a first hinge assembly 618, and the second support 612 being hingedly attached to a second hinge assembly 620. The toilet seat assembly 600 also comprises a lid 604 which comprises a first lid support 614 and a second lid support 616, the first lid support 614 being attached to the first hinge assembly 618 and the second lid support 616 being attached to the second hinge assembly 620. The toilet seat assembly supports 610, 612, 614, 616 are each arcuate in shape. The first support 610 and the second support 612 each comprise a hollow interior cavity through which water tubes or electrical wires may be passed into the rinsing seat 602. The first hinge assembly 618 and the second hinge assembly 620 may comprise motors so that the movement of the rinsing seat 602 and the lid 604 is motorized. The motorized rinsing seat 602 and lid 604 would be particularly helpful to toilet users with a medical condition that prevents them from easily reaching, moving, or lifting objects. The use of motors also gives the toilet seat assembly 600 a capacity for autonomous function. For example, the motors may be controlled by a controller, which comprises a processor and a memory unit. The processor may be connected to seat sensors such as strain gauges, pressure transducers, or a combination thereof in the rinsing seat 602. The processor may be connected to proximity sensors in the rinsing seat 602 or in the lid 604. The processor may be connected to seat sensors that measure displacement of water in the toilet bowl such as ultrasonic sensors, laser range-finding sensors, infrared range-finding sensors, a machine vision system, or a combination thereof. Using these sensors, the processor may determine that a user is sitting on the rinsing seat 602, or otherwise using the toilet by monitoring connected sensors. When a user is detected to have finished using the toilet and is also detected to no longer be sitting on the toilet, the processor may use the controller to automatically close the toilet lid 604 and perform a toilet flush. The processor may also monitor sensors to determine when a user intends to urinate into the toilet from a standing position and automatically lift the rinsing seat 602 using motors in the first hinge assembly 618 and the second hinge assembly 620. Seat sensors may be used by the processor to dynamically vary the volume of rinse water dispensed through the rinsing seat 602. For example, the seat sensors may be used to determine a user's weight and then determine a volume of water to be dispensed in the rinse water through the rinsing seat 602 that is generally appropriate for a user of that weight. Thus, a 200 lb user will cause a greater volume of water to be dispensed to rinse the bowl than a 60 lb user based on a preprogrammed assumption that a 200 lb user generally deposits a greater volume of waste (thus increasing the volume and likelihood of excrement streak formation) in the toilet bowl than a 60 lb user would. Such a dynamically varying system allows for water conservation in the case of lighter users using the toilet. Greater volumes of water can be conserved if a machine vision system is used which would continuously monitor the toilet bowl surface and identify excrement streaks. The rinse water volume could be dynamically varied based on excrement streak size or length of excrement streak presence so that a greater volume of rinse water is only used when deemed necessary to remove larger excrement streaks. Alternatively, the seat sensors may dynamically vary the rinse water volume based on water displacement, thus dispensing greater volumes of water only when greater displacement (and thus a greater volume of deposited waste) is detected. The rinsing seat 602 may comprise a compressible membrane such that water stored in an annular cavity of the rinsing seat 602 is pressurized by the weight of a user sitting on the seat. The pressurized water could then be dispensed from the outlet nozzle openings 608 to rinse the bowl in conjunction with a flushing routine or independently of a flushing routine in order to clean a toilet bowl.

Figure 7:
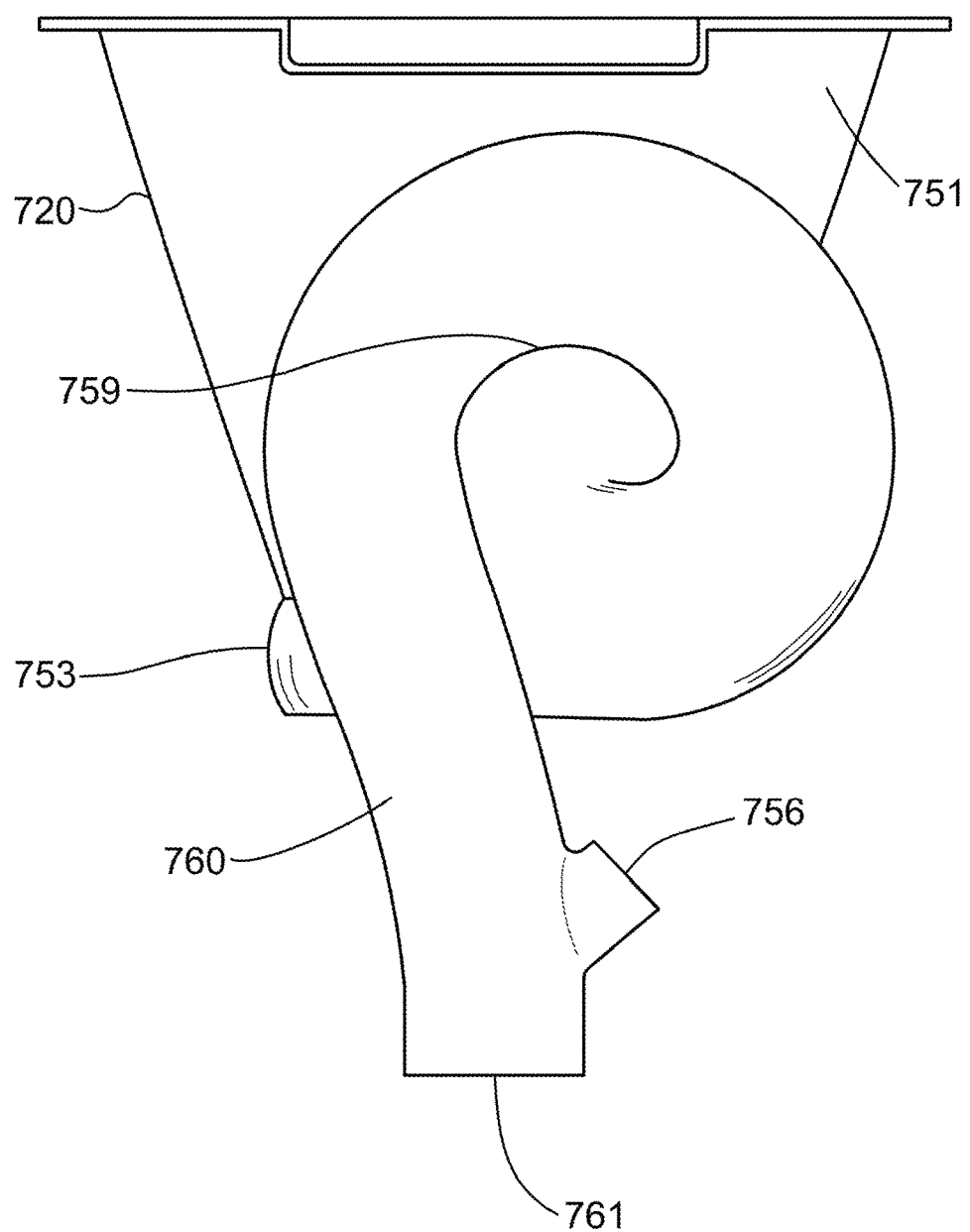
FIG. 7 shows a rear view of a toilet bowl and helical loop trapway.

FIG. 7 shows a bowl 751 and a substantially vertical looped tubular drain 750. The first end of the drain 750 exits the bowl 751 and forms a loop comprising a crest 759. The axis of the substantially vertical loop runs generally parallel to the front-to-back length of bowl 751, or generally perpendicular to the side-to-side width of the bowl 751. As depicted the vertical loop 750 is a left-hand or counterclockwise loop; alternatively, the vertical loop 750 may be a right-hand or clock-wise loop. A portion of the loop 750 may comprise a spiral, such as an Archimedean spiral. The drain may comprise a high-pressure jet 753 to assist in moving the contents of the bowl over the crest 759 of vertical loop to the second end of the drain 761. The vertical loop 750 may act as a siphon comprising a spillway 760 in removing the contents of the bowl 751 to the second end 761 adapted for connection to a sewer. The drain may comprise one or more ports 756. One of the ports 756 may intersect the drain at an angle of less than 90 degrees. The ports 756 may be connected to a hydraulic or pneumatic system. The tubular diameter of the vertical loop 750 may vary by approximately 20 percent or less in the direction of the sewer connection.

Figure 8:
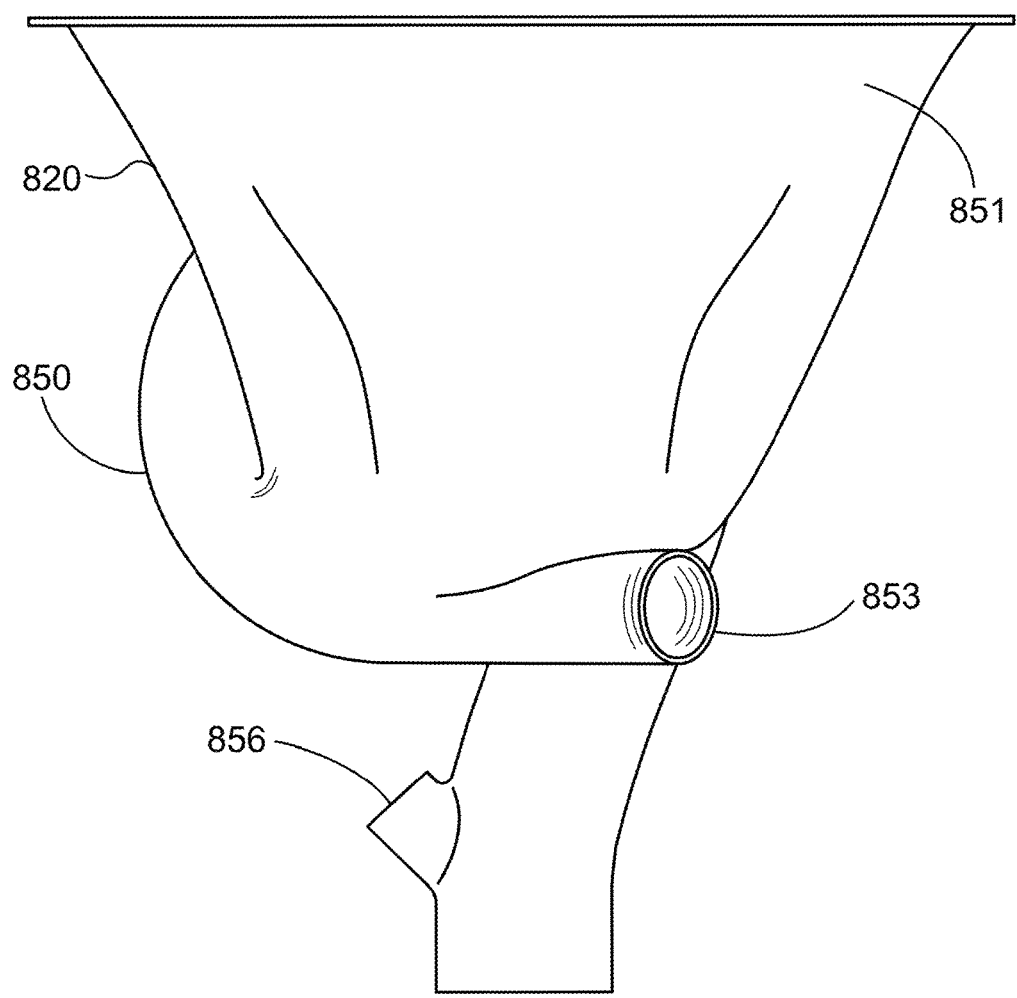
FIG. 8 shows a front view of a toilet bowl and helical loop trapway.

FIG. 8 shows a front view of the bowl 751 and the substantially vertical looped tubular drain 750 of FIG. 7. A bowl 851 is shown connected to a looped tubular drain 850 exiting the bowl, a hydraulic jet 853 directed toward the mouth of the drain, and a port 56. The axis of the tubular looped drain 850 runs generally parallel to the bowl 851, or generally perpendicular to the width of the bowl 851. As viewed from the front, the drain forms a right-hand loop 850.

Figure 9:
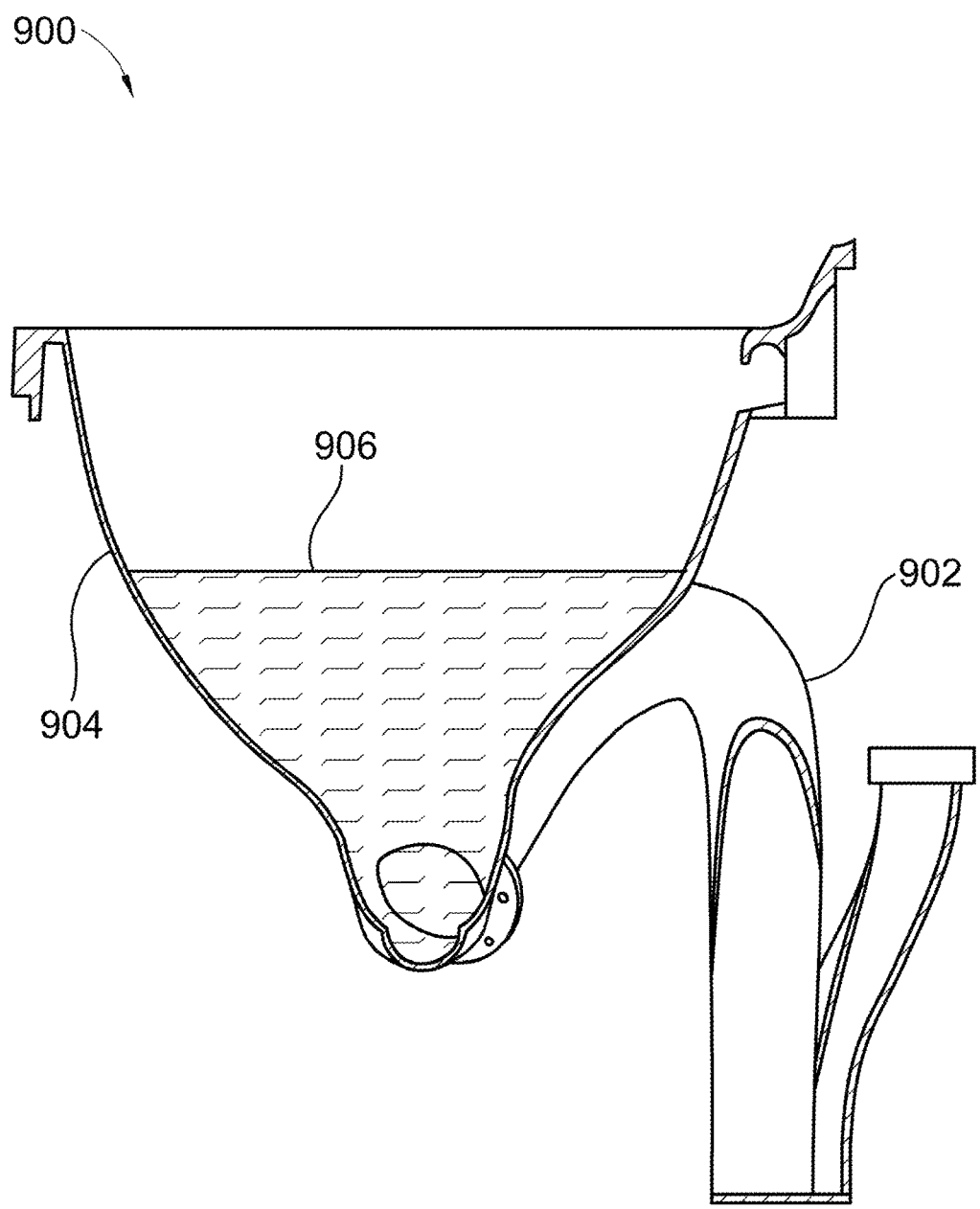
FIG. 9 shows a cross-sectional view of rimless toilet bowl and helical loop trapway.

FIG. 9 shows a cross-sectional view of a toilet module 900 of the present invention wherein a rimless toilet bowl is shown having a steep interior wall 904 and the toilet module is filled to a nominal water level 906. The nominal water level 906 represents the water level of a water reservoir in the toilet bowl used to receive human waste. As described heretofore, sensors may be used to measure the displacement of the reservoir water relative to the nominal water level in order to determine when a user is using the toilet and/or the volume of waste deposited into the toilet by a user. The toilet bowl is shown being connected to a helical loop drain 902.

Figure 10:
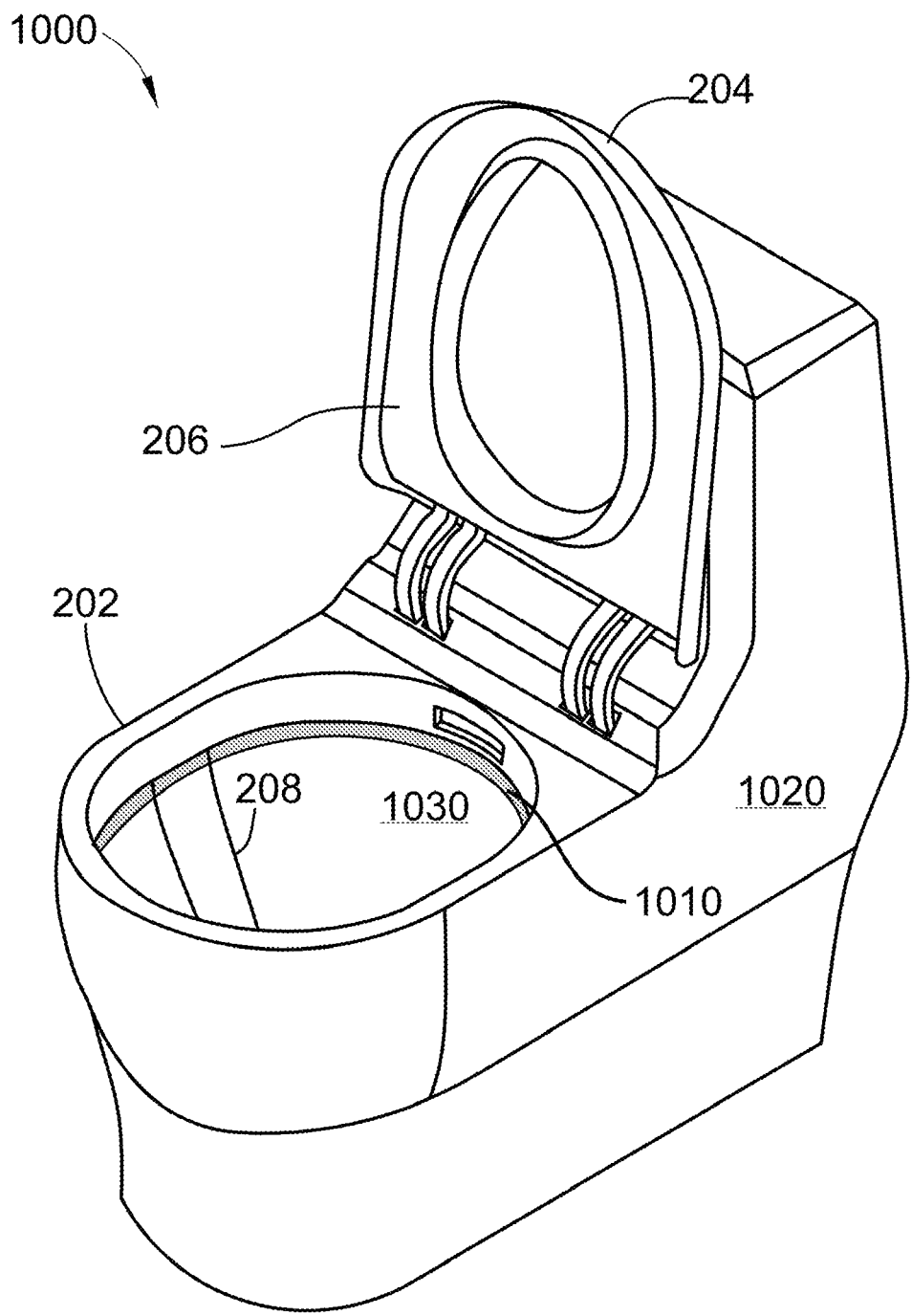
FIG. 10 shows a perspective view of a rimless toilet bowl with titanium dioxide and doped titanium dioxide coatings.

FIG. 10 shows toilet 1000 which is similar to the embodiment of FIG. 2. Toilet 1000 further includes ultraviolet light source 1010 encircling the upper circumference of titanium dioxide coated, rimless bowl 1010. In an example, ultraviolet light source 1030 may emit light at a wavelength that is equal to or less than about 520 nm. After flushing, the ultraviolet light source 1010 may be actuated and ultraviolet light may activate the antimicrobial properties of the titanium dioxide coating. In some embodiments, the ultraviolet light source is actuated by a switch as is known in the art. Prior to actuating ultraviolet light source 1010, the titanium dioxide coating is not antimicrobial. Consequently, microbes which may be analyzed in a medical toilet or used in a digester for producing clean energy are not killed. Only those microbes remaining behind in titanium dioxide coated, rimless bowl 1030 are killed and only after flushing. In contrast, surface 1020 is coated with doped titanium dioxide. The entire toilet 1000 other than titanium dioxide coated, rimless bowl 1030 may be covered with surface 1020. Doped titanium dioxide is antimicrobial without activation by ultraviolet light. Consequently, surface 1020 may be antimicrobial in the presence of the visible light of the room.

Doped titanium dioxide may be doped with a variety of elements including, but not limited to, one or more of the following: nitrogen, carbon, phosphorus, sulfur, fluorine, noble metals, and transition metals. In an example, carbon doped titanium dioxide may include carbon according to the formula $C—TiO_2$. In another example, nitrogen doped titanium dioxide may include nitrogen according to the formula $TiO_{2-x}N_x$. In another example, nitrogen doped titanium dioxide may include between about 0.5% and about 2% nitrogen. In yet another example, the doped titanium dioxide may include both fluorine and nitrogen.

Figure 11:
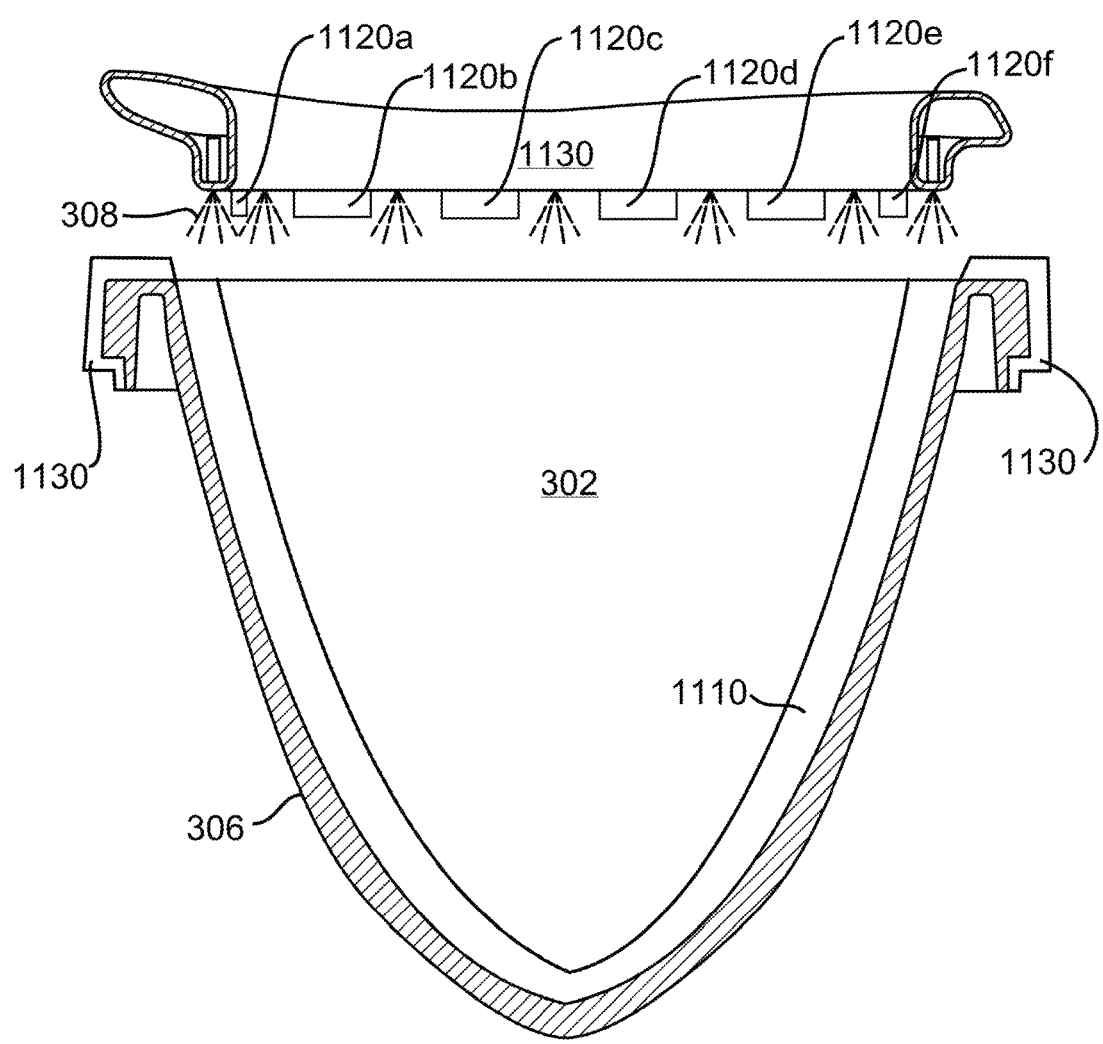
FIG. 11 shows a rinsing seat dispensing rinse water into a rimless, titanium dioxide coated bowl and ultraviolet lights in the seat.

FIG. 11 is a cross-sectional view similar to that of FIG. 3. FIG. 11 shows another embodiment of a rimless toilet in which titanium dioxide and doped titanium dioxide are used for their antimicrobial properties as discussed herein. In the embodiment of FIG. 11, steep interior wall 306 is coated with titanium dioxide coating 1110. Ultraviolet light sources 1120*a*, 1120*b*, 1120*c*, 1120*d*, 1120*e*, 1120*f* are connected to the lower side of the rinsing seat. Ultraviolet light sources 1120*a-f* are shown between orifices which may dispense rinse water 308. The ultraviolet light activates the antimicrobial properties of titanium dioxide coating 1110. Surface 1130 covers the rinsing seat and the outer surface of rimless bowl 302 imparting antimicrobial properties to these parts in the presence of visible light.

The apparatuses disclosed herein may be embodied in other specific forms without departing from their spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

We claim:

1. A toilet comprising:
a rimless bowl comprising:
  an inner surface;
  a titanium dioxide coating disposed on the inner surface; and
  an ultraviolet light source, wherein the ultraviolet light source directs ultraviolet light towards the inner surface of the rimless bowl;
a seat comprising an annular cavity, said annular cavity comprising inlet ports connected to a remote water source, the seat further comprising a plurality of outlet nozzles arranged circumferentially and directed to the rimless bowl, the plurality of outlet nozzles being connected to the annular cavity; and
wherein
a rinsing volume of water is dispensed out of the seat through the plurality of outlet nozzles; and
a doped titanium dioxide coating, wherein the doped titanium dioxide coating is adhered to at least one surface exterior to the rimless bowl.

2. The toilet of claim 1, wherein the ultraviolet light source is disposed on an upper circumference of the rimless bowl.

3. The toilet of claim 1, wherein the ultraviolet light source is disposed on a lower surface of the seat.

4. The toilet of claim 1, wherein the doped titanium dioxide coating comprises nitrogen according to the following formula: $TiO_{2-x}N_x$.

5. The toilet of claim 4, wherein the doped titanium dioxide coating comprises between about 0.5% and about 2% nitrogen.

6. The toilet of claim 1, wherein the ultraviolet light source emits light at wavelengths of less than about 520 nm.

7. The toilet of claim 1, wherein the doped titanium dioxide coating comprises carbon according to the following formula: $C—TiO_2$.

8. The toilet of claim 1, wherein the doped titanium dioxide coating comprises one or more of the following list: phosphorus, sulfur, and fluorine.

9. The toilet of claim 1, wherein the doped titanium dioxide coating comprises fluorine and nitrogen.

10. The toilet of claim 1, wherein the doped titanium dioxide coating comprises at least one noble metal.

11. The toilet of claim 1, wherein the doped titanium dioxide coating comprises at least one transition metal.

12. The toilet of claim 1, wherein the ultraviolet light source is actuated by a switch.

13. The toilet of claim 1, wherein the annular cavity further comprises a volume sufficient to store water and flush the toilet using the stored water and a water jet below a nominal water level of the toilet for initiating a flush.

14. The toilet of claim 1, wherein the remote water source is pressurized, the annular cavity further comprises a pressurized line, and the pressurized line is capable of dispensing pressurized water out of the outlet nozzles.

15. The toilet of claim 14, wherein the remote water source is a pressurized utility line of a building.

16. The toilet of claim 1, wherein the seat further comprises one or more arcuate supports, each of said one or more supports being hingedly attached to a hinge assembly.

17. The toilet of claim 16, wherein the one or more arcuate supports each comprise an interior cavity connected to the inlet ports, each interior cavity being connected to the remote water source.

18. The toilet of claim 1, further comprising a water tank, said water tank storing and dispensing a flushing volume of water into a helical loop trapway, and wherein the flushing volume of water and the rinsing volume of water are independently controlled such that the rinsing volume of water may be dispensed while the flushing volume of water is not being dispensed.

19. The toilet of claim 1, wherein the outlet nozzles comprise oscillating spray nozzles.

20. The toilet of claim 1, wherein the rinsing volume of water is dispensed from the plurality of outlet nozzles in an overlapping pattern.

* * * * *